(12) United States Patent
Sherman et al.

(10) Patent No.: US 8,151,624 B2
(45) Date of Patent: Apr. 10, 2012

(54) METHOD FOR MEASURING SURFACE SMOOTHNESS OF HAIR

(75) Inventors: Faiz Fiesal Sherman, Mason, OH (US); Holly Lynn Krigbaum, Cincinnati, OH (US); Vladimir Gartstein, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 784 days.

(21) Appl. No.: 12/207,522

(22) Filed: Sep. 10, 2008

(65) Prior Publication Data

US 2009/0071228 A1 Mar. 19, 2009

Related U.S. Application Data

(60) Provisional application No. 60/993,747, filed on Sep. 14, 2007.

(51) Int. Cl.
*G01N 3/56* (2006.01)
(52) U.S. Cl. .............................................. 73/9
(58) Field of Classification Search .................... None
See application file for complete search history.

(56) References Cited

U.S. PATENT DOCUMENTS

| | | | |
|---|---|---|---|
| 4,167,869 A * | 9/1979 | Gikas | 73/862.541 |
| 4,711,244 A | 12/1987 | Kuzara | |
| 4,719,930 A * | 1/1988 | Gross et al. | 132/205 |
| 4,966,158 A | 10/1990 | Honma et al. | |
| 4,967,038 A | 10/1990 | Gevins et al. | |
| 5,001,436 A | 3/1991 | Scot et al. | |
| 5,131,417 A * | 7/1992 | Zaias et al. | 132/204 |
| 6,817,222 B2 | 11/2004 | Day et al. | |
| 7,402,135 B2 | 7/2008 | Leveque et al. | |
| 7,472,577 B2 * | 1/2009 | Shibuichi et al. | 73/9 |
| 7,928,739 B2 | 4/2011 | Sherman et al. | |
| 2002/0010556 A1 * | 1/2002 | Marapane et al. | 702/32 |
| 2003/0233861 A1 * | 12/2003 | Woolston et al. | 73/9 |
| 2005/0048021 A1 * | 3/2005 | Salem et al. | 424/70.14 |
| 2007/0054261 A1 | 3/2007 | Sherman et al. | |
| 2007/0056859 A1 | 3/2007 | Sherman et al. | |
| 2007/0185392 A1 | 8/2007 | Sherman et al. | |
| 2007/0190006 A1 | 8/2007 | Sherman et al. | |
| 2007/0191694 A1 | 8/2007 | Sherman et al. | |
| 2007/0213606 A1 | 9/2007 | Sherman et al. | |

FOREIGN PATENT DOCUMENTS

| | | | |
|---|---|---|---|
| JP | 62273433 | * | 11/1987 |
| JP | 2003-144005 A | | 5/2003 |

OTHER PUBLICATIONS

Brandstetter, J., *Effect of surface roughness on friction in fibre-bundle pull-out tests*, Composites Science and Technology vol. 65, Issue 6, May 2005, pp. 981-988.

Gupta, Prabhat K., *Simple Method for Measuring the Friction Coefficient of Thin Hairs*, Journal of the American Ceramic Society (1991) 74 (7), 1692-1694.

* cited by examiner

*Primary Examiner* — Robert R Raevis
(74) *Attorney, Agent, or Firm* — James T. Fondriest; Angela K. Haughey

(57) ABSTRACT

A method for measuring the surface smoothness of hair comprising the steps of:
a) providing a means for measuring hair surface smoothness;
b) using said means for measuring hair a surface smoothness to obtain a measured surface smoothness value for said hair; and
c) correlating said surface smoothness value to a surface smoothness descriptors.

12 Claims, No Drawings

METHOD FOR MEASURING SURFACE SMOOTHNESS OF HAIR

CROSS REFERENCE TO RELATED APPLICATION

The present application claims priority to provisional U.S. application Ser. No. 60/993,747 filed Sep. 14, 2007.

FIELD OF THE INVENTION

The present invention relates generally to methods for measuring the smoothness of fibers. More specifically, the invention relates to methods of measuring the smoothness of human hair fibers. Another aspect of the present invention is a method of measuring hair conditions of a consumer and recommending an appropriate hair product to treat the related hair conditions.

BACKGROUND OF THE INVENTION

It is widely recognized that a link between hair friction and consumer assessments of its visible/tactile characteristics exists. Hair friction is an important physical property, responsible for many visible and tactile characteristics of the hair array. Combing ease is linked to friction and friction also plays a role in how consumers perceive hair conditions and feel.

A widely accepted method for measuring smoothness and softness of hair is combing friction. In practice combing force is measured in the laboratory using a hair switch connected to a load cell. The action of combing, which can be automated or manual stroking, pulls downward on the switch to register a recorded force. In many cases, the hairs being combed will become entangled and cause the comb to snarl and lock as it is pulled through a sample. The only remedy for such entanglement is to use greater force to pull the comb through the tangled sample of hairs. Such forceful pulling causes inconsistencies in measurements and generally requires considerable repetition in order to achieve relatively consistent results.

Another widely used method is generally known as INSTRONO® sled friction. The INSTRON® sled coefficient of friction fixture device is commercially available from INSTRON® as Catalog Number 2810-005. This friction testing method employs an INSTRON® to measure the frictional force as a weighted sled is pulled across the surface of a treated hair bundle. The friction is controlled by the sled surface material (against the hair) and normal force applied. INSTRON® sled friction is generally considered an industry standard when used to compare treatments and evaluate new actives. Nevertheless, this method has demonstrated discrepancies when used to predict or correlate with in vivo consumer use data. This equipment is also too large and impractical to use in vivo, which further prevents such testing from achieving optimal results.

Based on the foregoing, there is a need for a method of assessing the condition of hair in a manner suitable to assess the quality of growing human hair (in vivo). Particularly, there is a need for a method of assessing the condition of hair smoothness and providing consumers with hair treatment recommendations based upon the condition of the hair.

SUMMARY OF THE INVENTION

It has been discovered that the condition of hair can be readily assessed, and a product for treating the condition of the hair can be recommended by conducting a method for measuring the surface smoothness of hair comprising the steps of:

a) providing a means for measuring hair surface smoothness;

b) using said means for measuring hair surface smoothness to obtain a measured surface smoothness value for said hair; and c) correlating said surface smoothness value to a surface smoothness descriptors.

One embodiment particularly relates the aforementioned method wherein subsequently, or instead of, step c), the step of using said correlated hair surface smoothness value to select at least one appropriate hair treatment, and optionally applying said appropriate hair treatment to said hair is added.

These and other features, aspects and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

As used herein, "surface smoothness" refers to the friction force associated with the surface texture of a fibrous material, ie. human hair.

According to the present invention, methods are described for measuring the surface smoothness of fibrous materials. The hairs herein may be any types of hairs or fibers, including wool, cotton, silk, rayon, or other natural or synthetic hairs. The hairs may also be selected from animal hairs such as camel hair, goat hair, horse hair, or the like. Hereinafter, the hairs will be referred to in terms of human hair.

In the case of human hair, surface smoothness is an important indicator of the overall health of hair. A measurement of hair smoothness can be used to quantify various physical and cosmetic characteristics of hair. Surface smoothness can specifically be a strong indicator of hair dryness, tightness, damage, and soil. Various products are commercially available which may treat the different hair types which may be identified based upon the smoothness of hair. Accordingly, the present invention provides methods of assessing the smoothness of hair, in order to better identify products which may best treat the various types of hair conditions.

One aspect of the invention is to provide a method for measuring surface smoothness of hair which comprises the steps of providing a means for measuring hair surface smoothness, using the means for measuring hair surface smoothness to obtain a measured surface smoothness value for the hair, and correlating the surface smoothness value to a surface smoothness descriptor.

The means for measuring hair surface smoothness is a handheld friction sensor comprising a clamping member and a load cell. As discussed hereinabove, a key indicator of the overall condition of hair is friction. Load cells are well known in the art for measuring friction, and can be readily incorporated into a variety of devices. Generally, load cells which are used for measuring smoothness of hair are large, and are therefore restricted to laboratory or industrial applications. For specific information relating to load cells and the measurement of the friction coefficient of hairs, see Prabhat K. Gupta, *Simple Method for Measuring the Friction Coefficient of Thin Hairs*, Journal of the American Ceramic Society (1991) 74 (7), 1692-1694; or J. Brandstetter, *Effect of surface roughness on friction in fibre-bundle pull-out tests*, Composites Science and Technology Volume 65, Issue 6, May 2005, Pages 981-988. In order to measure friction more easily, it has been found that applying a small load cell to a handheld device is very practical and efficient means for measuring the smoothness of hair. As is taught in the aforementioned references, in order to maintain a normal force against the hair, upon which the smoothness measurement is to be taken, a clamping member may be provided. Such a configuration creates a clamping member/hair/load cell interface upon which measurements can be generated. In one embodiment, the load cell and/or clamping member may further include disposable pads (ie. a foam pad) in order to maintain a sanitary surface upon which to take measurements. A device comprising a clamping member suitable for compacting a bundle of hair is disclosed in U.S. application Ser. No. 11/823,894.

In a second step, the means for measuring hair surface smoothness is used to obtain a measured surface smoothness value for the hair sample. A bundle of hair is placed between the clamping member and the load cell, and the clamping member is closed, which creates a substantially constant normal force against the hair sample and load cell. The device is pulled across the bundle of hair at a substantially constant rate, and the friction of the material creates a voltage in the load cell, which is correlated to a hair smoothness value based upon the measured coefficient of friction. The device should be pulled in the direction from the root to tip of the hair sample. It has been found that acceptable smoothness value measurements of hair samples, according to the method herein, are generally in the range from about $\mu N=10$ to about $\mu N=500$. As used herein, $\mu$=static friction coefficient, N=normal force (generally exerted by the device's clamping member), and F=hair smoothness value, according to the formula, "$\mu N=F$". In one embodiment, the surface smoothness value is displayed on an LED display. In another embodiment, the measured smoothness value is stored in a programmable integrated circuit.

In a third step, the aforementioned surface smoothness value is correlated to a surface smoothness descriptor of the hair sample. The descriptor is then displayed on a screen, such as an LCD display. For example, the surface smoothness value of the second step is correlated to a predetermined descriptor of surface smoothness of the hair sample. The descriptors are associated with differing levels of smoothness based upon the measured surface smoothness value. For example, a sample which demonstrates a relatively high level of friction (and a low level of smoothness) may have an associated descriptor such as, "low", "rough", "dry", "brittle", or the like. A sample demonstrating a relatively average level of friction may have an associative descriptor such as, "normal", "average", "typical", "common", "standard", "medium", "intermediate", and the like. A sample demonstrating a relatively low level of friction (and a high level of smoothness) may have an associative descriptor such as, "high", "smooth", "soft", "sleek", "above average", and the like. Generally, any words, pictures, colors (ie. red to signify damage, yellow to signify average smoothness, and green to signify exceptional smoothness), or numbered grade scales which depict increasing or decreasing friction or smoothness of hair may be used.

In succession, or in the alternative to the third step above, the surface smoothness value is correlated to at least one recommended appropriate hair treatment. The recommended appropriate hair treatment is then displayed on a screen, such as an LCD display. As used herein, an "appropriate hair treatment" is a chemical composition, or non-chemical treatment, which provides or restores hair with the physical or cosmetic characteristics desired by a consumer. Exemplary hair treatment chemical compositions may include, without limitation, lotions, creams, gels, tonics, sprays, pastes, powder, mousses, shampoos, conditioners, oils, colorants, and biomedical and dermatological treatments. Nonlimiting examples of non-chemical treatments include, waxes treatments, protein serums, ionic treatments, plant extract treatments, and non-chemical straightening balms. Generally, the recommended appropriate hair treatment associates increasing surface friction with increasing conditioning treatment recommendations.

According the method herein, it may is necessary to compare the measured sample of hair to a predetermined category of hair. These categories are defined by their tendency to exhibit friction. For instance, based upon the type of hair being measured, three categories: high surface friction, moderate surface friction and low surface friction could be predetermined.

Hair of various types may then be assigned to one of these predetermined categories according to relevant factors. These factors may be selected from ethnic origin (for instance if the hair is of European, Asian or African origin); waviness (whether the hair is straight, wavy or curly); whether the hair has been previously subjected to treatments (perming, bleaching or coloring). Thus, this aspect of the invention is based, at least in part, on the recognition that surface smoothness of hair depends not only upon damage levels but on other hair characteristics.

Within each category is an associated standard average smoothness value of hair. This measurement is an illustration of the average surface friction expected to be generated by a sample of hair in the defined category when subjected to the method described above.

According to the method herein, the hair sample to be tested, which may be a hair switch but is generally hair growing on the head of a consumer, is assigned to one of the predefined categories according to the factors discussed above. In this way, a relative measurement of overall smoothness of specific hair types may be provided based upon a baseline predetermined average smoothness value measured for each category of hair.

The method of the invention is then carried out on the sample to be tested, generally in substantially the same manner as carried out to generate the standard average smoothness value. The surface smoothness value generated is displayed as a trace on a screen and this sample trace is compared with the standard average smoothness value of the predetermined hair type. It can then be assessed whether the hair sample is more or less damaged than would be expected from the characteristics above.

Various hair types, even within the aforementioned categories of hair types, are known to have varying levels of fiber-to-fiber friction associated with them. As this system assesses friction based upon surface smoothness of hair, inconsistent friction assessments due to fiber-to-fiber interactions, rather than due to the condition of the hair fiber surfaces, is eliminated. Varying degrees of friction associated with various types of hair are described in U.S. Pat. No. 6,817,222.

The method herein can be used by a consumer directly but is preferably applied by an operative or adviser, for instance in a store or salon. It is contemplated that after the assessment has been made appropriate treatment for the hair may further be proposed and optionally applied to the consumer's head in the store or salon.

Commercially, the method herein can used for measuring hair conditions on the head of a consumer, by conducting the following steps:

a. providing a device for measuring hair surface smoothness;

b. using said device to obtain hair surface smoothness values from head of said consumer;

c. correlating said hair surface smoothness value to a hair condition descriptor for said consumer; and d. providing a product recommendation based upon said hair condition descriptor to said consumer.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for measuring the surface smoothness of hair comprising the steps of:
   a) providing a means for measuring hair surface smoothness;
   b) using said means for measuring hair surface smoothness to obtain a measured surface smoothness value for said hair; and
   c) correlating said surface smoothness value to a surface smoothness descriptor;
   wherein said means for measuring hair surface smoothness is a handheld device comprising a clamping member and a load cell; and
   wherein said clamping member further comprises a replaceable pad.

2. A method according to claim 1, wherein said surface smoothness value is measured by placing a bundle of hair between said clamping member and said load cell, closing said clamping member, and pulling said means for measuring hair surface smoothness across said bundle of hair.

3. A method according to claim 2, wherein said means for measuring hair surface smoothness is pulled in the root to tip direction of said bundle of hair.

4. A method according to claim 1, wherein said surface smoothness descriptor is selected from the group consisting of words, pictures, colors, and numbered grade scales which depict increasing or decreasing friction or smoothness of hair.

5. A method for measuring the surface smoothness of hair comprising the steps of:
   a) providing a means for measuring hair surface smoothness;
   b) using said means for measuring hair surface smoothness to obtain a measured surface smoothness value for said hair; and
   c) correlating said surface smoothness value to an appropriate hair treatment recommendation;
   wherein said means for measuring hair surface smoothness is a handheld device comprising a clamping member and a load cell; and
   wherein said clamping member further comprises a replaceable pad.

6. A method according to claim 5, wherein said hair treatment is selected from the group consisting of chemical compositions and non-chemical treatments.

7. A method according to claim 6, wherein said non-chemical treatment is selected from the group consisting of a wax treatment, protein serums, ionic treatments, plant extract treatments, and non-chemical straightening balms.

8. A method according to claim 6, wherein said chemical compositions are selected from the group consisting of lotions, creams, gels, tonics, sprays, pastes, powder, mousses, shampoos, conditioners, oils, colorants, and biomedical and dermatological treatments.

9. A method according to claim 6, wherein said hair surface smoothness value associates increasing surface friction with increasing conditioning treatment recommendations.

10. A method according to claim 5, further comprising the step of applying said appropriate hair treatment to the hair.

11. A method according to claim 5, further comprising the step of correlating said surface smoothness value to a surface smoothness descriptors.

12. A method for measuring hair conditions on the head of a consumer, said method comprising the steps of:
   a. providing a device for measuring hair surface smoothness;
   b. using said device to obtain hair surface smoothness values from the head of said consumer;
   c. correlating said hair surface smoothness value to a hair condition descriptor for said consumer; and
   d. providing a product recommendation based upon said hair condition descriptor to said consumer;
   wherein said device for measuring hair surface smoothness is a handheld device comprising a clamping member and a load cell; and
   wherein said clamping member further comprises a replaceable pad.

* * * * *